United States Patent
Nuttall et al.

(10) Patent No.: US 6,794,360 B2
(45) Date of Patent: Sep. 21, 2004

(54) TREATMENT OF ALLERGIC RHINITIS

(75) Inventors: Patricia Anne Nuttall, Culham (GB); Guido Christiaan Paesen, Jericho (GB)

(73) Assignee: Evolutec Limited, Oxford (GB)

( * ) Notice: Subject to any disclaimer, the term of this patent is extended or adjusted under 35 U.S.C. 154(b) by 0 days.

(21) Appl. No.: 10/087,195

(22) Filed: Mar. 1, 2002

(65) Prior Publication Data
US 2002/0193306 A1 Dec. 19, 2002

Related U.S. Application Data

(63) Continuation of application No. PCT/GB00/03287, filed on Aug. 24, 2000.

(30) Foreign Application Priority Data

Sep. 1, 1999 (GB) .............................................. 9920673

(51) Int. Cl.⁷ ........................ A61K 38/00; A61K 38/16; C07K 7/00; C07K 14/00; C07K 17/00

(52) U.S. Cl. ............................. 514/2; 514/12; 530/300; 530/324; 530/325; 530/350; 530/855; 530/858

(58) Field of Search ....................... 514/2, 12; 530/300, 530/324, 325, 350, 855, 858

(56) References Cited

U.S. PATENT DOCUMENTS 6,617,312 B1 * 9/2003 Paesen et al. ................. 514/21

FOREIGN PATENT DOCUMENTS

| GB | 2 283239 A | * | 6/1995 |
| WO | WO 97/44451 | | 11/1997 |
| WO | WO 99/27104 | | 6/1999 |

* cited by examiner

Primary Examiner—Christopher R. Tate
Assistant Examiner—Kailash C. Srivastava
(74) Attorney, Agent, or Firm—Klauber & Jackson

(57) ABSTRACT

The invention relates to the discovery that various proteins isolated from ticks are effective in the treatment and prevention of allergic rhinitis. These proteins may most suitably be applied to an effected area and are thus effective to treat this condition and to ameliorate its symptoms.

6 Claims, 8 Drawing Sheets

FIG. 1
Vacs of Life Study: Histamine binding protein
Histamine Nasal Challenge
Weight of Anterior Nasal Secretions (grams)

| Subject | \\ | Histamine (mg/ml) | | | | |
|---|---|---|---|---|---|---|
| | 0.5 | 1.0 | 2.0 | 4.0 | 8.0 | |
| PH | | | | | | |
| Pre | 0.023 | 0.022 | 0.294 | 0.456 | --- | |
| Post | 0.095 | 0.077 | 0.071 | 0.229 | --- | |
| JW | | | | | | |
| Pre | 0.451 | 0.323 | 0.303 | 0.286 | --- | |
| Post | 0.060 | 0.060 | 0.238 | 0.133 | 0.328 | |
| KC | | | | | | |
| Pre | 0.454 | 0.378 | 0.374 | 0.579 | 0.175 | |
| Post | 0.245 | 0.288 | 0.236 | 0.249 | --- | |

FIG. 2
Vacs of Life Study: Histamine binding protein
Histamine Nasal Challenge
Nasal Airways Resistance (kPa/L/sec)

Histamine (mg/ml)

| Subject | B | PVL | PS | 0.5 | 1.0 | 2.0 | 4.0 | 8.0 |
|---|---|---|---|---|---|---|---|---|
| PH |  |  |  |  |  |  |  |  |
| Pre | 0.193 | --- | 0.181 | 0.203 | 0.498 | 0.461 | 0.543 | 8.0 |
| Post | 0.235 | 0.185 | 0.190 | 0.187 | 0.250 | 0.297 | 0.317 | --- |
| JW |  |  |  |  |  |  |  |  |
| Pre | 0.174 | --- | 0.162 | 0.182 | 0.204 | 0.242 | 0.414 | --- |
| Post | 0.131 | 0.172 | 0.223 | 0.228 | 0.254 | 0.287 | 0.444 | 0.538 |
| KC |  |  |  |  |  |  |  |  |
| Pre | 0.190 | --- | 0.184 | 0.211 | 0.245 | 0.314 | 0.321 | 0.960 |
| Post | 0.207 | 0.214 | 0.228 | 0.245 | 0.288 | 0.236 | 0.249 | 0.843 |

B = Baseline    PVL = post Vacs of Life    PS = Post saline

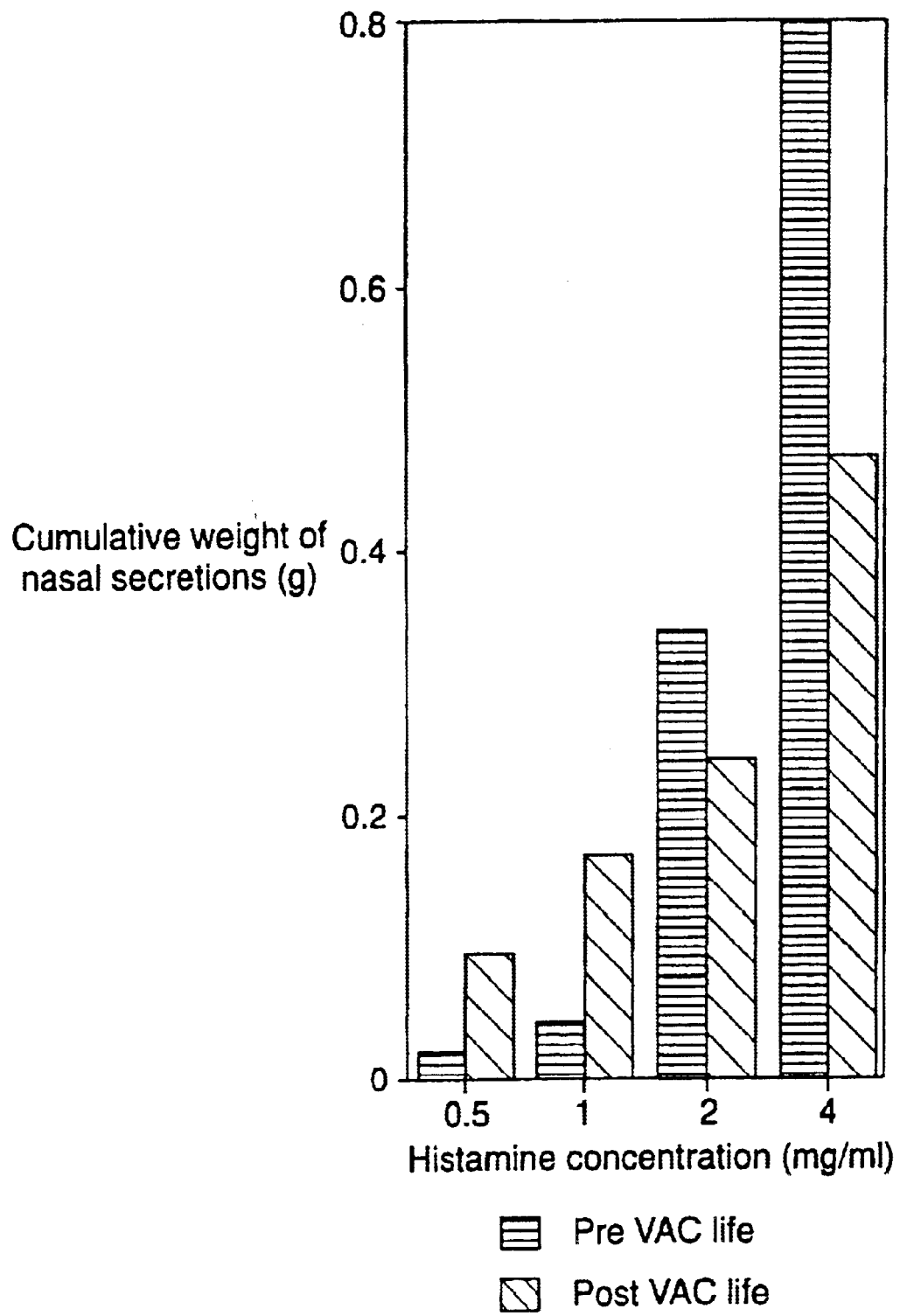

Nasal histamine challenge on subject JW

Nasal histamine challenge on subject KC

Nasal histamine challenge on subject PH

Nasal histamine challenge on subject JW

*Nasal histamine challenge on subject KC*

SEQUENCE LISTING

```
<160> NUMBER OF SEQ ID NOS: 8

<210> SEQ ID NO 1
<211> LENGTH: 4
<212> TYPE: PRT
<213> ORGANISM: arthropod
<220> FEATURE:
<221> NAME/KEY: VARIANT
<222> LOCATION: 1
<223> OTHER INFORMATION: Xaa = Asp
<221> NAME/KEY: VARIANT
<222> LOCATION: 1
<223> OTHER INFORMATION: Xaa= Glu
<221> NAME/KEY: VARIANT
<222> LOCATION: 4
<223> OTHER INFORMATION: Xaa= Lys
<221> NAME/KEY: VARIANT
<222> LOCATION: 4
<223> OTHER INFORMATION: Xaa= Arg

<400> SEQUENCE: 1

Xaa Ala Trp Xaa
 1

<210> SEQ ID NO 2
<211> LENGTH: 4
<212> TYPE: PRT
<213> ORGANISM: arthropod

<400> SEQUENCE: 2

Asp Ala Trp Lys
 1

<210> SEQ ID NO 3
<211> LENGTH: 5
<212> TYPE: PRT
<213> ORGANISM: arthropod

<400> SEQUENCE: 3

Gln Asp Ala Trp Lys
 1               5

<210> SEQ ID NO 4
<211> LENGTH: 4
<212> TYPE: PRT
<213> ORGANISM: arthropod
<220> FEATURE:
<221> NAME/KEY: VARIANT
<222> LOCATION: 1
<223> OTHER INFORMATION: Xaa = Tyr
<221> NAME/KEY: VARIANT
<222> LOCATION: 1
```

```
<223> OTHER INFORMATION: Xaa= Cys
<221> NAME/KEY: VARIANT
<222> LOCATION: 2
<223> OTHER INFORMATION: Xaa= Glu
<221> NAME/KEY: VARIANT
<222> LOCATION: 2
<223> OTHER INFORMATION: Xaa= Asp
<221> NAME/KEY: VARIANT
<222> LOCATION: 3
<223> OTHER INFORMATION: Xaa= Leu
<221> NAME/KEY: VARIANT
<222> LOCATION: 3
<223> OTHER INFORMATION: Xaa= Ile
<221> NAME/KEY: VARIANT
<222> LOCATION: (3)...(0)
<223> OTHER INFORMATION: Xaa= Phe

<400> SEQUENCE: 4

Xaa Xaa Xaa Trp
 1

<210> SEQ ID NO 5
<211> LENGTH: 4
<212> TYPE: PRT
<213> ORGANISM: arthropod
<220> FEATURE:
<221> NAME/KEY: VARIANT
<222> LOCATION: 1
<223> OTHER INFORMATION: Xaa = Tyr
<221> NAME/KEY: VARIANT
<222> LOCATION: 1
<223> OTHER INFORMATION: Xaa= Cys

<400> SEQUENCE: 5

Xaa Glu Leu Trp
 1

<210> SEQ ID NO 6
<211> LENGTH: 172
<212> TYPE: PRT
<213> ORGANISM: FS-HBP1

<400> SEQUENCE: 6

Asp Lys Pro Val Trp Ala Asp Glu Ala Ala Asn Gly Glu His Gln Asp
 1               5                  10                  15

Ala Trp Lys His Leu Gln Lys Leu Val Glu Glu Asn Tyr Asp Leu Ile
                20                  25                  30

Lys Ala Thr Tyr Lys Asn Asp Pro Val Trp Gly Asn Asp Phe Thr Cys
            35                  40                  45

Val Gly Thr Ala Ala Gln Asn Leu Asn Glu Asp Glu Lys Asn Val Glu
        50                  55                  60

Ala Trp Phe Met Phe Met Asn Asn Ala Asp Thr Val Tyr Gln His Thr
65                  70                  75                  80

Phe Glu Lys Ala Thr Pro Asp Lys Met Tyr Gly Tyr Asn Lys Glu Asn
                85                  90                  95

Ala Ile Thr Tyr Gln Thr Glu Asp Gly Gln Val Leu Thr Asp Val Leu
            100                 105                 110

Ala Phe Ser Asp Asp Asn Cys Tyr Val Ile Tyr Ala Leu Gly Pro Asp
        115                 120                 125

Gly Ser Gly Ala Gly Tyr Glu Leu Trp Ala Thr Asp Tyr Thr Asp Val
    130                 135                 140

Pro Ala Ser Cys Leu Glu Lys Phe Asn Glu Tyr Ala Ala Gly Leu Pro
145                 150                 155                 160

Val Arg Asp Val Tyr Thr Ser Asp Cys Leu Pro Glu
```

<210> SEQ ID NO 7
<211> LENGTH: 171
<212> TYPE: PRT
<213> ORGANISM: FS-HBP 2

<400> SEQUENCE: 7

```
Asn Gln Pro Asp Trp Ala Asp Glu Ala Ala Asn Gly Ala His Gln Asp
 1               5                  10                  15

Ala Trp Lys Ser Leu Lys Ala Asp Val Glu Asn Val Tyr Tyr Met Val
            20                  25                  30

Lys Ala Thr Tyr Lys Asn Asp Pro Val Trp Gly Asn Asp Phe Thr Cys
        35                  40                  45

Val Gly Val Met Ala Asn Asp Val Asn Glu Asp Glu Lys Ser Ile Gln
    50                  55                  60

Ala Glu Phe Leu Phe Met Asn Asn Ala Asp Thr Asn Met Gln Phe Ala
65                  70                  75                  80

Thr Glu Lys Val Thr Ala Val Lys Met Tyr Gly Tyr Asn Arg Glu Asn
                85                  90                  95

Ala Phe Arg Tyr Glu Thr Glu Asp Gly Gln Val Phe Thr Asp Val Ile
            100                 105                 110

Ala Tyr Ser Asp Asp Asn Cys Asp Val Ile Tyr Val Pro Gly Thr Asp
        115                 120                 125

Gly Asn Glu Glu Gly Tyr Glu Leu Trp Thr Thr Asp Tyr Asp Asn Ile
    130                 135                 140

Pro Ala Asn Cys Leu Asn Lys Phe Asn Glu Tyr Ala Val Gly Arg Glu
145                 150                 155                 160

Thr Arg Asp Val Phe Thr Ser Ala Cys Leu Glu
                165                 170
```

<210> SEQ ID NO 8
<211> LENGTH: 182
<212> TYPE: PRT
<213> ORGANISM: MS-HBP 1

<400> SEQUENCE: 8

```
Asn Pro Thr Trp Ala Asn Glu Ala Lys Leu Gly Ser Tyr Gln Asp Ala
 1               5                  10                  15

Trp Lys Ser Leu Gln Gln Asp Gln Asn Lys Arg Tyr Tyr Leu Ala Gln
            20                  25                  30

Ala Thr Gln Thr Thr Asp Gly Val Trp Gly Glu Glu Phe Thr Cys Val
        35                  40                  45

Ser Val Thr Ala Glu Lys Ile Gly Lys Lys Leu Asn Ala Thr Ile
    50                  55                  60

Leu Tyr Lys Asn Lys His Leu Thr Asp Leu Lys Glu Ser His Glu Thr
65                  70                  75                  80

Ile Thr Val Trp Lys Ala Tyr Asp Tyr Thr Thr Glu Asn Gly Ile Lys
                85                  90                  95

Tyr Glu Thr Gln Gly Thr Arg Thr Gln Thr Phe Glu Asp Val Phe Val
            100                 105                 110

Phe Ser Asp Tyr Lys Asn Cys Asp Val Ile Phe Val Pro Lys Glu Arg
        115                 120                 125

Gly Ser Asp Glu Gly Asp Tyr Glu Leu Trp Val Ser Glu Asp Lys Ile
    130                 135                 140

Asp Lys Ile Pro Asp Cys Cys Lys Phe Thr Met Ala Tyr Phe Ala Gln
```

```
                    -continued 145                 150                 155                 160
Gln Gln Glu Lys Thr Val Arg Asn Val Tyr Thr Asp Ser Ser Cys Lys
                165                 170                 175

Pro Ala Pro Ala Gln Asn
            180
```

TREATMENT OF ALLERGIC RHINITIS

This is a continuation of PCT/GB00/03287, filed Aug. 24, 2000.

The present invention relates to the discovery that various proteins isolated from ticks are effective in the treatment and prevention of allergic rhinitis. These proteins may most suitably be applied to an affected area and are effective to treat this condition and to ameliorate its symptoms.

Allergic rhinitis is the medical term given to the inflammation of the nasal mucosa caused by allergens such as pollen or dust. There are two general types of allergic rhinitis, seasonal and perennial. Seasonal allergic rhinitis is normally referred to as hay fever and is usually caused by mould or pollen. Perennial allergic rhinitis is usually caused by an inherent sensitivity to one or more types of allergen. This condition generally continues throughout the year or for as long as the patient is exposed to the allergen. The condition is thought to affect more than 15% of the population of the western world.

Both types of allergic rhinitis involve a type 1 (IgE-mediated) hypersensitivity that leads to inflammation. This inflammation is thought to be caused by an excessive degranulation of mast cells and of blood-borne basophils in response to certain allergens. This leads to increased IgE levels and the concomitant release of inflammatory mediators, such as histamine, and of chemotactic factors, such as cytokines, prostaglandins and leukotrienes, that result in a localised inflammatory reaction.

In many cases, prevention of allergic rhinitis can be maximised by avoiding contact with the causative allergen, since even the best medical therapies currently available are ineffective in the face of a high allergen load. However, this is not always possible or practical.

A number of interventional approaches are widely used, including the use of intranasal vasoconstrictors, intranasal and systemic antihistamines, intranasal glucocorticoids, mast cell stabilisers, such as cromolyn compounds, and oral decongestants. One problem with some of the more well-established treatments is that they have a sedative effect, so causing a decrease in patient performance, alertness and cognitive function. Although some non-sedating histamine H1 antagonists are now available, there is a great need for the identification of other non-sedative agents that are effective in the treatment of this condition.

Conventional $H_1$ receptor antagonists are widely used as antihistamine agents for treating allergic reactions including allergic rhinitis (hay fever), urticaria, insect bites and drug hypersensitivities. $H_1$ receptor antagonists target the redness and inflammation that is associated with these conditions. However, there are numerous undesirable effects of the $H_1$ receptor antagonists currently used. When used for purely antihistamine actions, all of the effects on the central nervous system (CNS) are unwanted. When used for their sedative or anti-emetic actions, some of the CNS effects such as dizziness, tinnitus and fatigue are unwanted. Excessive doses can cause excitation and may produce convulsions in children. The peripheral anti-muscarinic actions are always undesirable. The commonest of these is dryness of the mouth, but blurred vision, constipation and retention of urine can also occur. Unwanted effects not related to the drug's pharmaceutical action are also seen. Thus, gastrointestinal disturbances are fairly common while allergic dermatitis can follow topical application of these drugs.

$H_2$ receptor antagonists are also used as antihistamine agents. These agents target the itching that is associated with the condition as a result of activation of certain aspects of the nervous system.

It can therefore be seen that drugs used to control the actions of histamine are not always effective. The reasons why they may have limited efficacy may relate to the specificity of these drugs for only a sub-class of histamine receptors, particularly when a certain class of conditions requires interference with a larger class of receptors. Indeed, it is now known that there are a large number of different chemoattractants and vasoactive substances implicated in allergic rhinitis, liberated not only by mast cells but also by eosinophils and other cells, that produce undesirable symptoms in patients with allergic disorders.

There is thus a great need for agents that are effective in ameliorating the symptoms of this condition, but that do not generate the side-effects that detract from their attractiveness as therapeutic compounds.

Molecules that are capable of binding to histamine have previously been identified in blood-feeding ectoparasites, such as ticks. For example, a salivary nitric oxide-carrying haeme protein (nitrophorin) of the triatome bug *Rhodnius prolixus* has been found to bind histamine (Ribeiro & Walker, 1994). The isolation of a family of vasoactive amine binding proteins from ticks is described in co-pending International Patent Application No. PCT/GB97/01372, owned by the Applicant for the present invention. The contents of this application are incorporated into the present application in their entirety. These proteins bind to histamine and are closely related to one another. Some of these molecules also bind to serotonin. These molecules differ markedly from any of the $H_1$, $H_2$ or $H_3$ receptor families and appear to bind to histamine in a different manner.

The present invention is based on the discovery that these tick proteins, and molecules based on their structure, are effective in the treatment of allergic rhinitis.

SUMMARY OF THE INVENTION

According to the present invention there is provided the use of a histacalin protein in the manufacture of a medicament for the treatment or prevention of allergic rhinitis.

The present invention also provides a method for the treatment or prevention of allergic rhinitis which comprises administering to a subject an effective amount of a histacalin protein.

The term "histacalin protein" in the present application denotes:

(a) any vasoactive amine binding protein that binds specifically to a vasoactive amine with a dissociation constant of less than $10^{-7}$M and which belongs to the same protein family as the proteins MS-HBP1, FS-HBP1 and FS-HBP-2 disclosed in co-pending International Patent Application No. PCT/GB97/01372 wherein a protein is considered to belong to this protein family if the primary, mature monomer sequence of the protein has no more than 260 amino acids and at least 30 of the amino acids in the protein's complete sequence are conserved as identical residues in an alignment of that protein and the proteins MS-HBP1, FS-HBP1 and FS-HBP-2, the alignment preferably having been obtained using GCG's pileup command (Program Manual for the Wisconsin Package, 1994; gap creating penalty=3; gap extension penalty=1, scoring matrix Blosum62.cmp, pileup carried out using the endweight option);

(b) a protein from a haematophagous arthropod that binds specifically to histamine with a dissociation constant less than $10^{-7}$ M and which contains the sequence motifs D/E A W K/R (preferably DAWK, more preferably QDAWK) and Y/C E/D L/I/F W (preferably Y/C ELW);

(c) a natural biological variant, such as an allelic variant or a geographical variant, of a protein as defined in (a) or (b) above;

(d) a functional equivalent of a protein as defined in (a), (b) or (c) above that contains single or multiple amino-acid substitution(s), addition(s), insertion(s) and/or deletion(s) from the wild type protein sequence and/or substitutions of chemically-modified amino acids that do not affect the biological function of binding to its respective vasoactive amine;

(e) an active fragment of a protein as defined in (a), (b), (c) or (d) above, wherein "active fragment" denotes a truncated protein that retains the biological function of binding to its respective vasoactive amine; and (f) a fusion protein comprising a protein as defined in (a), (b), (c), (d) or (e) above fused to a peptide or other protein, such as a label, which may be, for instance, bioactive, radioactive, enzymatic or fluorescent, or an antibody.

An alignment of the proteins MS-HBP1, FS-HBP1 and FS-HBP-2 obtained using GCG's pileup command (Program Manual for the Wisconsin Package, 1994; gap creating penalty=3; gap extension penalty=1, scoring matrix Blosum62.cmp, pileup carried out using the endweight option) is shown in Table 1 below.

TABLE I

SEQUENCE COMPARISON OF FS-HBP1 (top line), FS-HBP2 (middle line) and MS-HBP1 (bottom line). Identical residues are marked "=" below the three lines of sequence. The sequences were aligned as described above

| | | | | | | | | | | | | | | | | | | | |
|---|---|---|---|---|---|---|---|---|---|---|---|---|---|---|---|---|---|---|---|
| D | K | P | V | W | A | D | E | A | A | N | G | E | H | Q | D | A | w | K | H |
| N | Q | P | D | W | A | D | E | A | A | N | G | A | H | Q | D | A | W | K | S |
| N |   | P | T | W | A | N | E | A | K | L | G | S | Y | Q | D | A | W | K | S |
|   |   | = |   | = | = |   | = | = |   |   | = |   |   | = | = | = | = | = | = |
| L | Q | K | L | V | E | E | N |   |   | Y | D | L | I | K | A | T | Y | K | N |
| L | K | A | D | V |   | E | N | V |   | Y | Y | M | V | K | A | T | Y | K | N |
| L | Q | Q |   |   | D | Q | N | K | R | Y | Y | L | A | Q | A | T | Q | T | T |
| = |   |   |   |   |   | = |   | = |   | = |   |   |   | = | = | = |   |   |   |
| D | P | V | W | G | N | D | F | T | C | V | G | T | A | A | Q | N | L | N | E |
| D | P | V | W | G | N | D | F | T | C | V | G | V | M | A | N | D | V | N | E |
| D | G | V | W | G | E | E | F | T | C | V | S | V | T | A | E | K | I | G |   |
| = |   | = | = | = |   |   | = | = | = | = |   |   |   | = |   |   |   |   |   |
| D | E | K | N | V | E | A | W | F | M | F | M | N | N | A | D | T | V | Y | Q |
| D | E | K | S | I | Q | A | E | F | L | F | M | N | N | A | D | T | N | M | Q |
|   | K | K | K | L | N | A | T | I | L | Y | K | N | K | H | L | T | D | L | K |
| H | T | F | E | K | A | T | P | D | K | M | Y | G | Y | N | K | E | N | A | I |
| F | A | T | E | K | V | T | A | V | K | M | Y | G | Y | N | R | E | N | A | F |
| E | S | H | E | T | I | T | V | W | K | A | Y | D | Y | T | T | E | N | G | I |
|   |   |   | = |   | = |   |   | = |   |   | = |   | = |   |   | = | = |   |   |
| T | Y | Q | T | E | D | G |   |   |   | Q | V | L | T | D | V | L | A | F | S |
| R | Y | E | T | E | D | G |   |   |   | Q | V | F | T | D | V | I | A | Y | S |
| K | Y | B | T | Q |   | G | T | R | T | Q | T | F | E | D | V | F | V | F | S |
|   | = |   | = |   |   | = |   |   |   | = |   |   |   | = | = |   |   |   | = |
| D |   | D | N | C | Y | V | I | Y | A | L | G | P | D | G | S | G | A | G |   |
| D |   | D | N | C | D | V | I | Y | V | P | G | T | D | G | N | E | E | G |   |
| D | Y | K | N | C | D | V | I | F | V | P | K | E | R | G | S | D | E | G | D |
| = |   |   | = | = |   | = | = |   |   |   |   |   |   | = |   |   |   | = |   |
| Y | E | L | W | A | T |   | D |   | Y | T | D | V | P | A | S | C | L | E | K |
| Y | E | L | W | T | T |   | D |   | Y | D | N | I | P | A | N | C | L | N | K |
| Y | E | L | W | V | S | E | D | K | I | D | K | I | P |   | D | C | C |   | K |
| = | = | = | = |   |   |   | = |   |   |   |   |   | = |   |   | = |   |   | = |
| F | N |   | E | Y |   | A | A | G | L | P |   | V | R | D | V | Y | T |   |   |
| F | N |   | E | Y |   | A | V | G | R | E |   | T | R | D | V | F | T |   |   |
| F | T | M | A | Y | F | A | Q | Q | Q | E | K | T | V | R | N | V | Y | T | D |
| = |   |   |   | = |   | = |   |   |   |   |   |   |   | = |   |   | = |   |   |
| S | D | C | L | P |   |   | E |   |   |   |   |   |   |   |   |   |   |   |   |
| S | A | C | L |   |   |   | E |   |   |   |   |   |   |   |   |   |   |   |   |
| S | S | C | K | P | A | P | A | Q | N |   |   |   |   |   |   |   |   |   |   |
| = |   | = |   |   |   |   |   |   |   |   |   |   |   |   |   |   |   |   |   |

Preferably, a protein is in the same family as the above proteins if it contains more than 40, more preferably more than 50, more preferably more than 60 residues, most preferably 70 residues or more which are identical as defined in a) above when aligned with the proteins shown in Table 1.

Preferably, the histacalin protein is derived from a blood-feeding ectoparasite, such as a leech, mosquito or tick. Most preferably, the histacalin protein is derived from a tick, in particular a species of hard tick such as *R. appendiculatus*, *I. ricinus* and *D. reticulatus*.

Preferably, a histacalin protein as defined in (a) above has at least 50%, more preferably at least 60% and most preferably 70% or more amino acid residues conserved as identical residues in an alignment of that protein with the proteins MS-HBP1, FS-EBP1 and FS-HBP2.

Preferably, a pharmaceutically-acceptable carrier is also used in the manufacture of the medicament according to the invention. Such a pharmaceutically-acceptable carrier is also preferably used in the method of the present invention.

Suitable pharmaceutically-acceptable carriers include carriers that do not themselves induce the production of antibodies that are harmful to the individual receiving the composition. Typically, suitable carriers are large, slowly metabolised macromolecules such as proteins, polysaccharides, polylactic acids, polyglycolic acids, polymeric amino acids, amino acid copolymers, lipid aggregates (such as oil droplets or liposomes) and inactive virus particles. Such carriers are well known to those of skill in the art.

Pharmaceutically-acceptable carriers in therapeutic compositions may also contain liquids such as water, saline, glycerol and ethanol. Additionally, auxiliary substances, such as wetting or emulsifying agents and pH buffering substances, may be present.

Optionally, one or more other, conventional antihistamine agents or anti-sedative agents may also be used in the manufacture of the medicament according to the invention. Such conventional antihistamine agents or anti-sedative agents may also be used in the method of the present invention. The inclusion of these agents allows a synergistic effect on allergic rhinitis.

Sometimes conventional antihistamine agents provide unwanted side-effects, such as drowsiness. In this eventuality, it may be advantageous to further include one or more anti-sedative agents in the manufacture of the medicament and in the method. Suitable anti-sedative agents are well known to those of skill in the art.

The histacalin proteins described above may be used for the treatment of any condition of allergic rhinitis. This term is meant to include both seasonal and perennial allergic rhinitis.

Treatment may be occasional, for example in the case of seasonal allergic rhinitis. The patient may in these cases apply the histacalin protein only when symptoms of allergic rhinitis appear or are likely to appear, for example, during conditions of high atmospheric pollen content.

Any mammalian patient is suitable for treatment by the method of the present invention. Preferably, the patient is human.

Patients who suffer from perennial allergic rhinitis may need to apply the histacalin protein continuously as a preventative measure. In order to ensure the application of an effective dose, the patient may need to apply the histacalin protein once, twice, three times or even four times daily.

The histacalin protein may be administered topically to the affected area by intra-nasal drops or aerosol spray or systemically by oral administration, such as in capsules or cartridges, or by injection.

Preferably, the histacalin proteins will be applied intranasally, in order that the nasal mucosa are exposed to them. The most suitable form of medicament for intranasal administration is generally an aerosol spray, examples of which may be found in the art (see, for example British National Formulary No. 37, March 1999: Drugs used in nasal allergy). The histacalin protein should be diluted in a suitable pharmaceutical carrier such as water or saline. Preferably, physiological saline, pH 7.2, is used.

The effective dose for a given treatment can be determined by routine experimentation and is within the judgement of the skilled person. For example, in order to formulate a range of dosage values, cell culture assays and animal studies can be used. The dosage of such compounds preferably lies within the dose that is therapeutically effective in 50% of the population, and that exhibits little or no toxicity at this level. For the purposes of the present invention, the term "therapeutically-effective" means that it produces a clinically significant reduction in nasal airway resistance and/or a reduction in the quantity of nasal mucus and/or a reduction in nasal pruritus.

For the purposes of the present invention, an effective dose is considered to be between 0.01 $\mu$g/kg and 50 $\mu$g/kg or, more typically, between 0.05 $\mu$g/kg and 10 $\mu$g/kg of the individual to which it is administered.

Preferably, for intranasal administration, the histacalin proteins are present in solution at between 0.1 $\mu$g/ml and 100 $\mu$g/ml, preferably between 0.1 $\mu$g/ml and 10 $\mu$g/ml, more preferably between 1 $\mu$g/ml and 8 $\mu$g/ml.

Various aspects and embodiments of the present invention will now be described in more detail by way of example with reference to the accompanying drawings, in which:

FIG. 1 shows a table of the data obtained for three volunteer subjects relating to nasal secretions;

FIG. 2 shows a table of the data obtained for three volunteer subjects relating to nasal airway resistance:

FIGS. 3a, 3b and 3c show the data for nasal secretions in graphical form for each individual subject.

It will be appreciated that modification of detail may be made without departing from the scope of the invention.

EXAMPLE

In this study, three subjects were challenged intranasally with histamine. The histamine concentrations used were 0.5 mg/ml, 1.0 mg/ml, 2.0 mg/ml, 4.0 mg/ml and, where necessary to achieve a 100% or greater increase in nasal airway resistance on the pre-treatment challenge, 8 mg/ml. One hundred microliters of each dose was administered to each nostril for each challenge.

Initially, baseline measurements were taken of the subjects' anterior nasal secretions. Nasal secretions were measured by asking subjects to blow their noses into pre-weighed paper handkerchiefs and then re-weighing them to calculate the weight of secretions produced.

Each subject was, then administered with a nasal histamine dose-response challenge. 45 minutes after the completion of the challenge, baseline measurements were repeated. Then a histacalin protein, EV504, was administered as a fresh solution of pre-weighed aliquots of histacalin in phosphate buffered saline. The solution was administered by dropping from a pipette into each nostril.

EV504 is an internal designation for the histamine binding protein MS-HBP1 described in PCT/GB97/01372. In the attached Figures it is referred to as VAC life or Histamine binding protein.

Figure 3B:
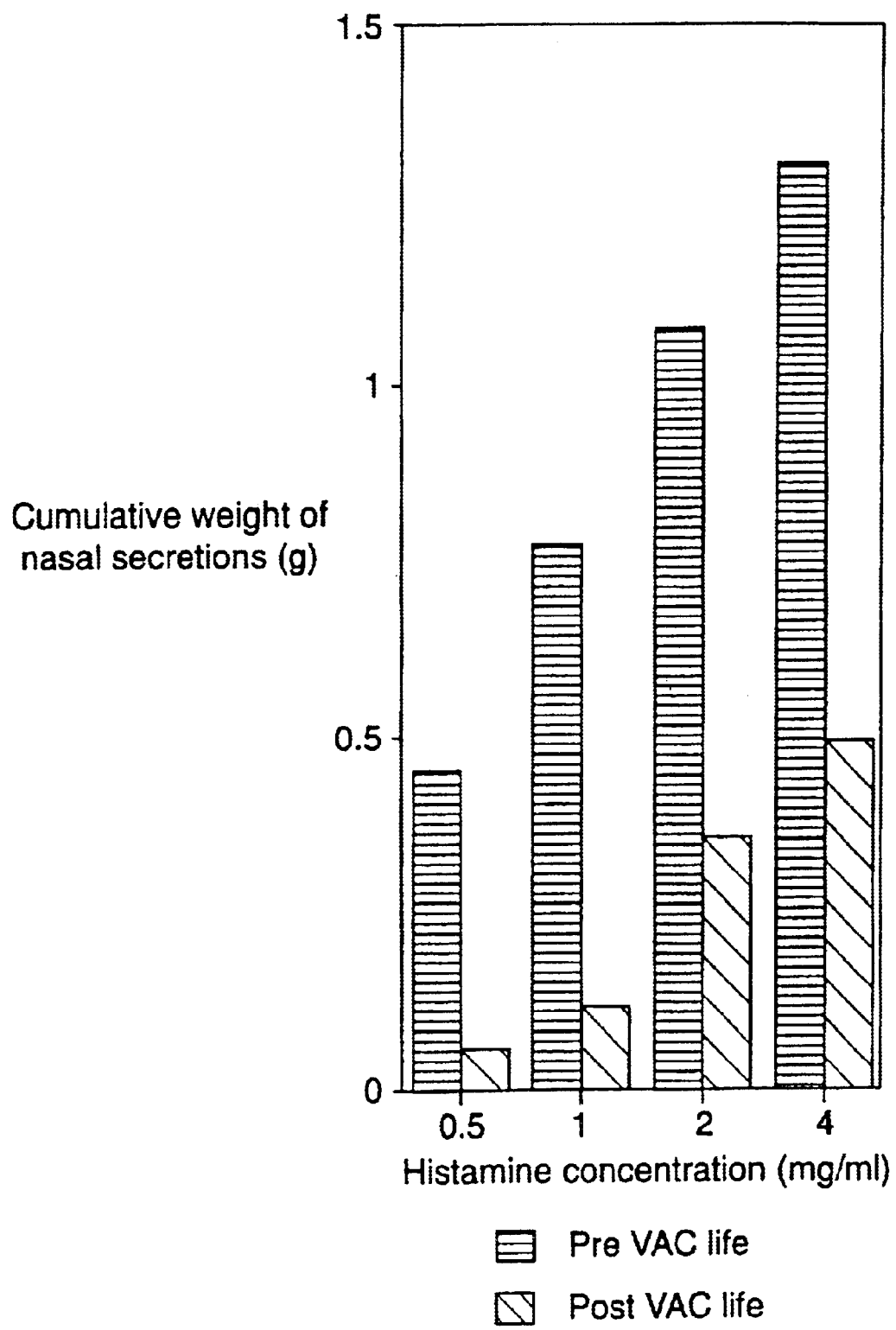
Figure 3C:
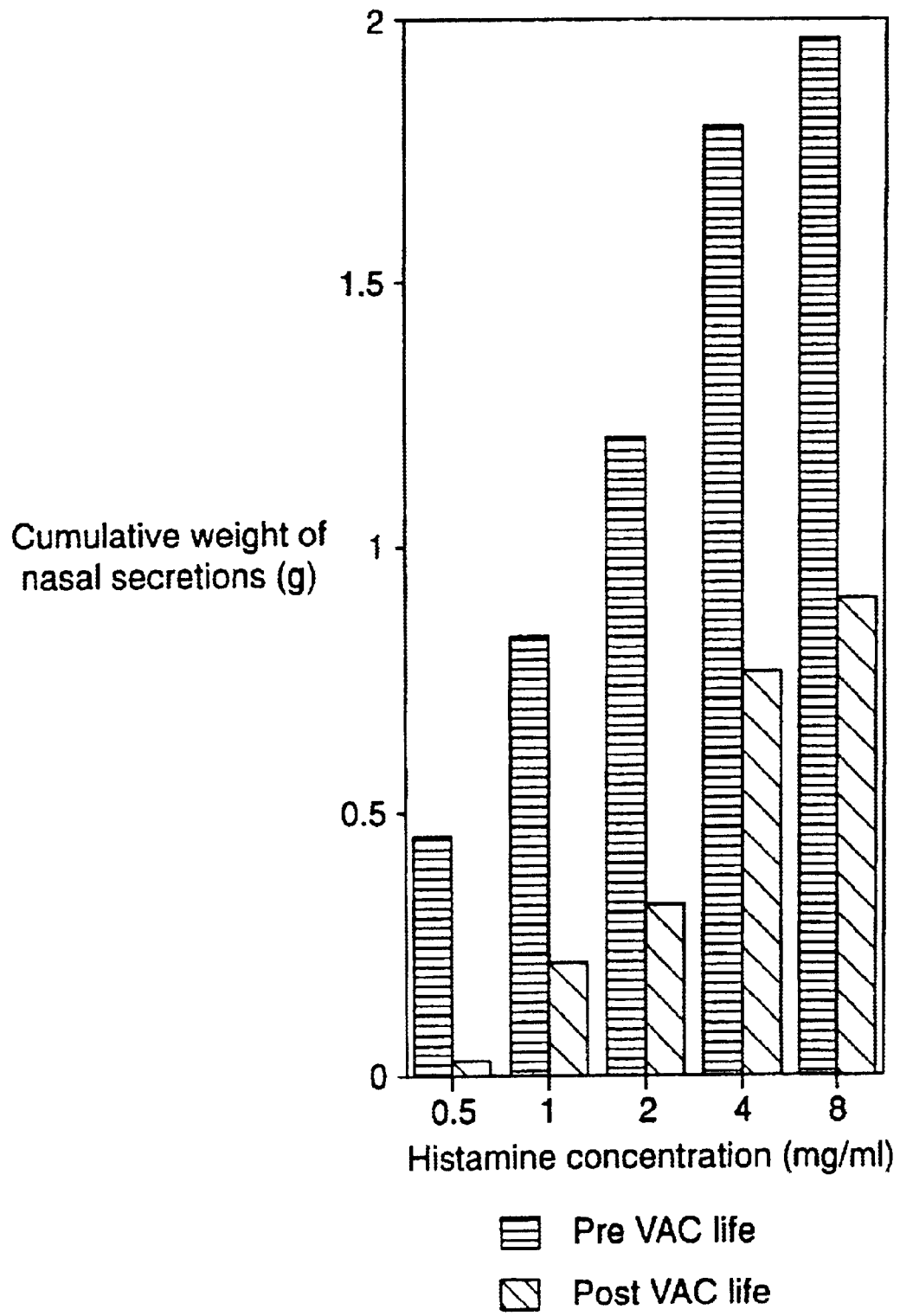

After a further 15 minutes, a repeat nasal histamine dose-response challenge was administered. The outcome measurements are recorded as total nasal airway resistance, as measured by active posterior rhinomanometry (placing inflatable balloons in the posterior nares and monitoring changes in pressure and volume), and by measurement of anterior nasal secretions, as measured by weight of expelled secretions. The anterior nasal secretions are represented as a cumulative total for the histamine challenges. These measurements are shown in FIGS. 1, 3*a*, 3*b* and 3*c*.

Figure 4A:
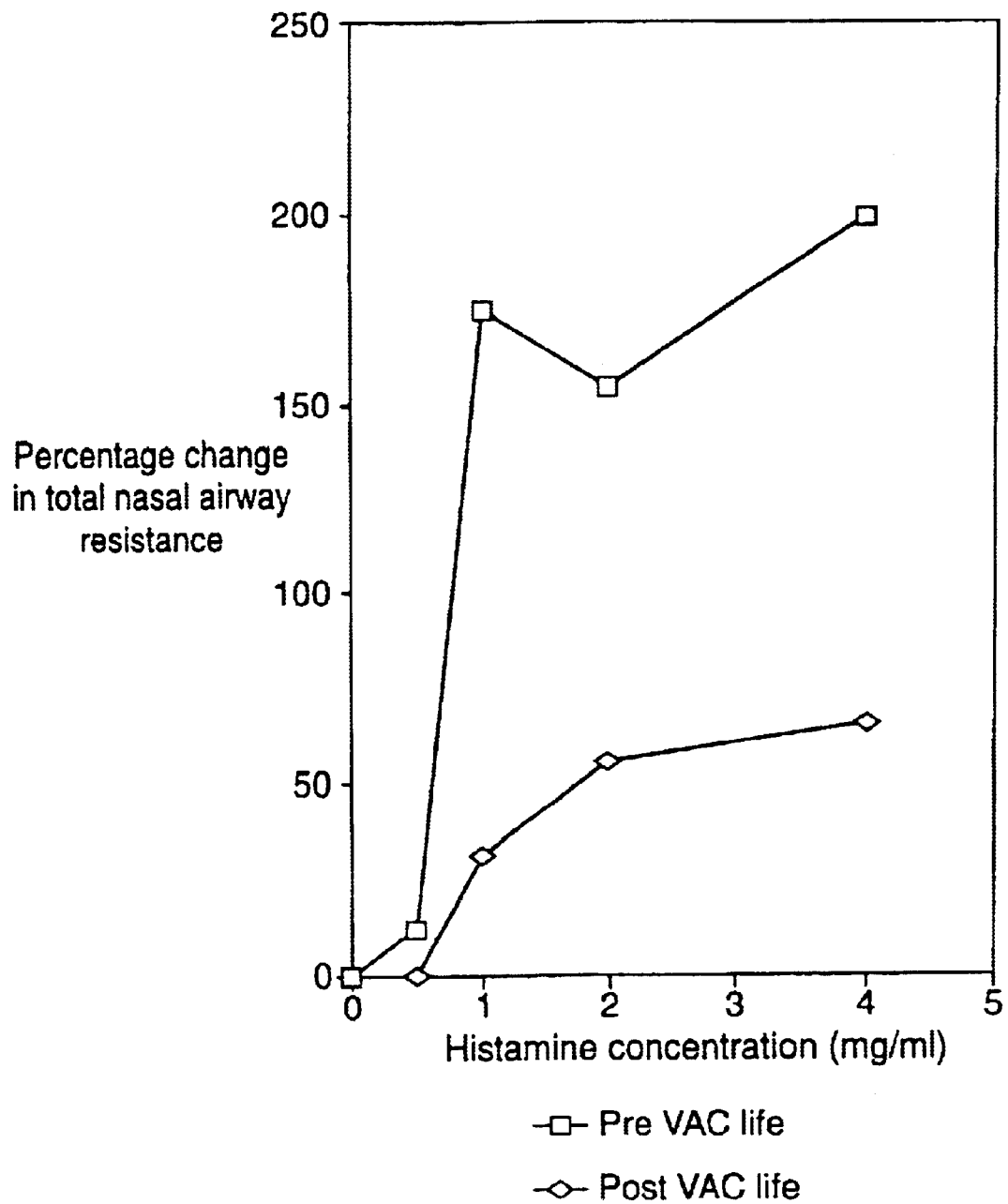
FIGS. 4a, 4b and 4c show the data for nasal airway resistance in graphical form for each individual subject.
Figure 4B:
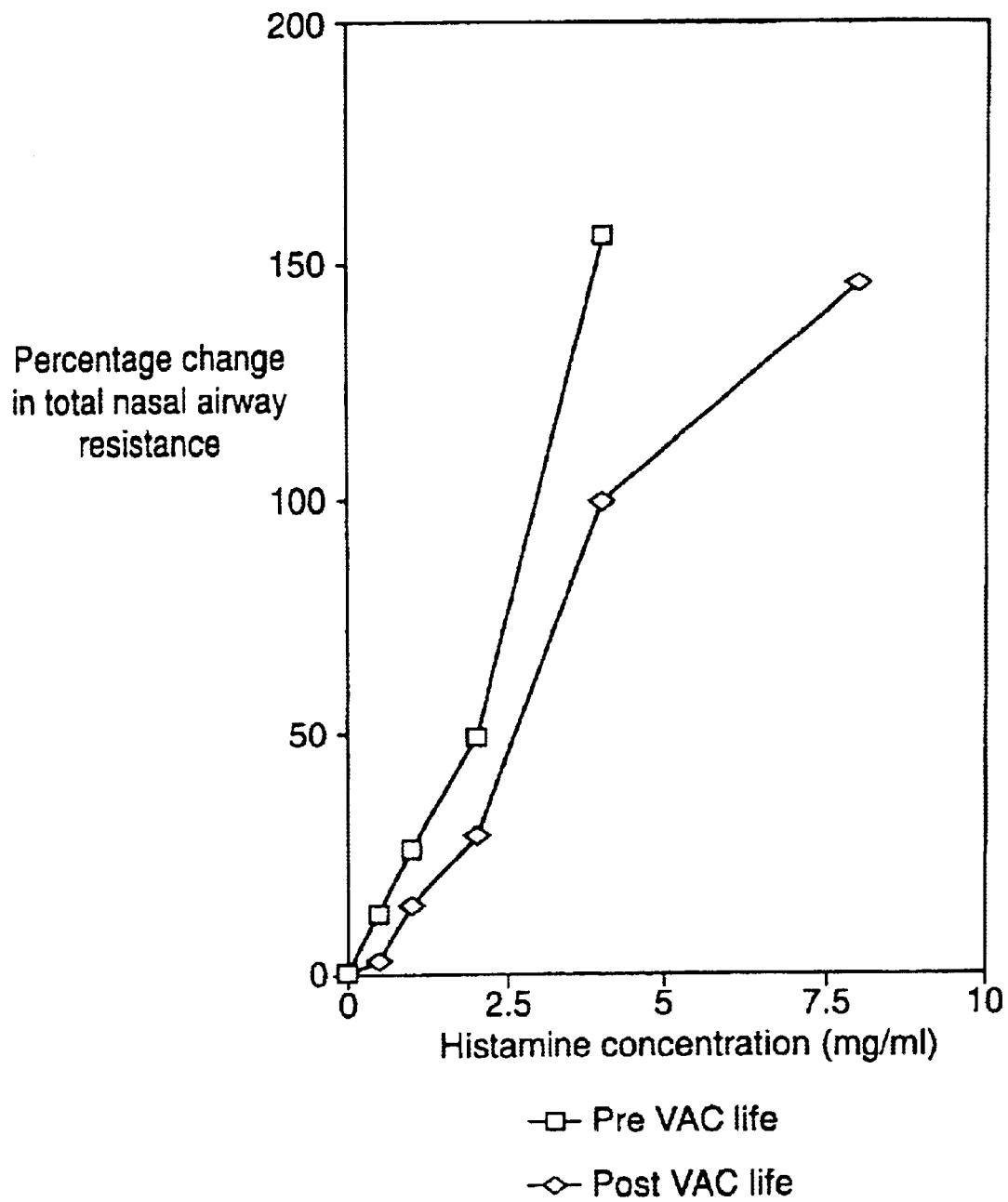
Figure 4C:
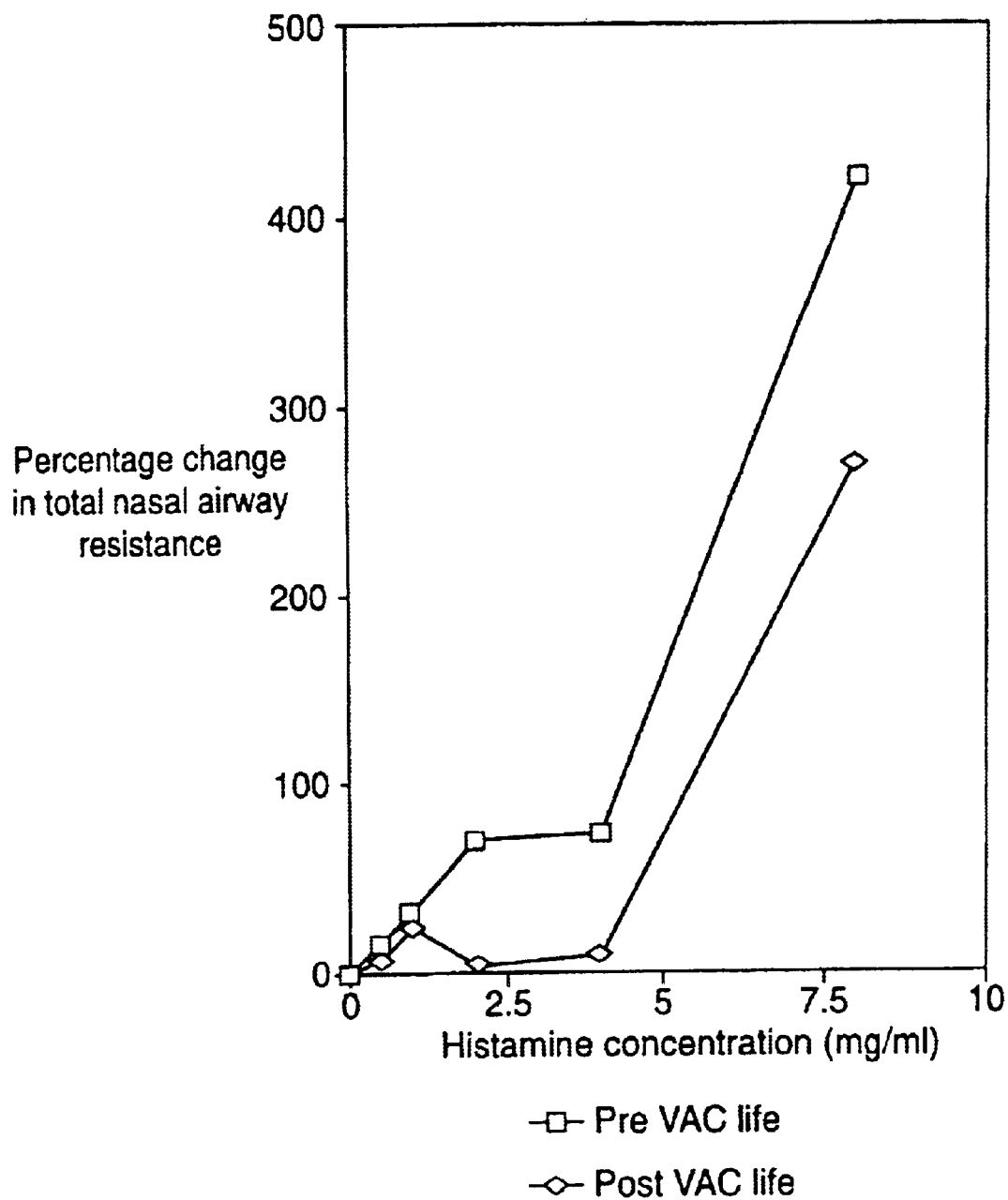

For FIGS. 2, 4*a*, 4*b* and 4*c*, the nasal airway resistance measured has been represented as a percent change from a saline challenge response (undertaken as the first challenge in the histamine dose-response challenge).

What is claimed is:

1. A method of treating or preventing allergic rhinitis comprising administering to a subject a histacalin protein in a therapeutically effective dosage.

2. A method according to claim 1, wherein said histacalin protein is from a blood feeding ectoparasite.

3. A method according to claim 2, wherein said histacalin protein is from a tick.

4. A method according to claim 1, wherein said histacalin protein is the MS-HBP1, FS-HBP1, FS-HBP2 or D.RET6 protein, a functional equivalent thereof or an active fragment thereof.

5. A method according to claim 1, wherein the subject is administered a medicament comprising said histacalin protein and a pharmaceutically acceptable excipient.

6. A method according to claim 1, wherein said allergic rhinitis is seasonal or perennial allergic rhinitis.

* * * * *